(12) United States Patent
Bruszewski et al.

(10) Patent No.: US 9,549,830 B2
(45) Date of Patent: Jan. 24, 2017

(54) EVERSIBLE BRANCH STENT-GRAFT AND DEPLOYMENT METHOD

(71) Applicant: Medtronic Vascular, Inc., Santa Rosa, CA (US)

(72) Inventors: Walter Bruszewski, Guerneville, CA (US); Masoumeh Mafi, Santa Rosa, CA (US); Shyam Nagasrinivasa, Santa Rosa, CA (US); Maria Acosta de Acevedo, Rohnert Park, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 14/614,531

(22) Filed: Feb. 5, 2015

(65) Prior Publication Data

US 2015/0173920 A1 Jun. 25, 2015

Related U.S. Application Data

(62) Division of application No. 12/055,083, filed on Mar. 25, 2008, now Pat. No. 8,974,518.

(51) Int. Cl.
| | |
|---|---|
| *A61F 2/06* | (2013.01) |
| *A61F 2/856* | (2013.01) |
| *A61F 2/07* | (2013.01) |
| *A61F 2/95* | (2013.01) |
| *A61F 2/89* | (2013.01) |

(52) U.S. Cl.
CPC ............... *A61F 2/856* (2013.01); *A61F 2/07* (2013.01); *A61F 2/89* (2013.01); *A61F 2002/061* (2013.01); *A61F 2002/065* (2013.01); *A61F 2002/075* (2013.01); *A61F 2002/9511* (2013.01)

(58) Field of Classification Search
CPC .... A61F 2/2418; A61F 2/2475; A61F 2/2412; A61F 2/07; A61F 2/856; A61F 2/954; A61F 2002/061; A61F 2002/075
See application file for complete search history.

(56) References Cited

U.S. PATENT DOCUMENTS

| | | | |
|---|---|---|---|
| 5,035,706 A * | 7/1991 | Giantureo | ............... A61F 2/86 606/198 |
| 5,387,235 A | 2/1995 | Chuter | |
| 5,456,713 A | 10/1995 | Chuter | |
| 5,693,084 A | 12/1997 | Chuter | |
| 5,709,713 A | 1/1998 | Evans et al. | |
| 5,720,776 A | 2/1998 | Chuter et al. | |
| 5,755,772 A * | 5/1998 | Evans | ...................... A61F 2/07 128/898 |
| 6,565,597 B1 | 5/2003 | Fearnot et al. | |

(Continued)

*Primary Examiner* — Thomas J Sweet
*Assistant Examiner* — Tiffany Shipmon (57) ABSTRACT

A method of deploying an eversible branch stent-graft includes deploying the eversible branch stent-graft into a main vessel such that a collateral opening in a main stent-graft of the eversible branch stent-graft is aligned with an ostium of a branch vessel emanating from the main vessel. A branch stent ring suture threaded though outer exposed crowns of an outer stent ring of the branch stent-graft is grasped and pulled through the collateral opening to evert the branch stent-graft into the branch vessel as a branch anchor suture is removed to release a protruding end of a branch stent-graft from a proximal end of the main stent-graft.

18 Claims, 4 Drawing Sheets

(56) References Cited

U.S. PATENT DOCUMENTS

| | | | |
|---|---|---|---|
| 2003/0199967 A1* | 10/2003 | Hartley | A61F 2/07 623/1.13 |
| 2005/0143806 A1 | 6/2005 | Phillips | |
| 2006/0276883 A1 | 12/2006 | Greenberg et al. | |
| 2007/0244542 A1 | 10/2007 | Greenan | |

* cited by examiner

EVERSIBLE BRANCH STENT-GRAFT AND DEPLOYMENT METHOD

RELATED APPLICATIONS

This application is a Division of and claims the benefit of U.S. patent application Ser. No. 12/055,083 filed Mar. 25, 2008, now allowed. The disclosures of which are herein incorporated by reference in their entirety.

BACKGROUND OF THE INVENTION

Field of the Invention

The present invention relates to an intra-vascular device and method. More particularly, the present invention relates to a device for treatment of intra-vascular diseases.

Description of Related Art

A conventional main (vessel) stent-graft typically includes a radially expandable reinforcement structure, formed from a plurality of annular stent rings, and a cylindrically shaped layer of graft material, sometimes called graft cloth, defining a lumen to which the stent rings are coupled. Main stent-grafts are well known for use in tubular shaped human vessels.

To illustrate, endovascular aneurysmal exclusion is a method of using a main stent-graft to exclude pressurized fluid flow from the interior of an aneurysm, thereby reducing the risk of rupture of the aneurysm and the associated invasive surgical intervention.

Main stent-grafts with custom side openings are sometimes fabricated to accommodate the particular vessel structure of each individual patient. Specifically, as the location of branch vessels emanating from a main vessel, e.g., having the aneurysm, varies from patient to patient, main stent-grafts are fabricated with side openings customized to match the position of the branch vessels of the particular patient. Branch stent-grafts are then deployed within the side openings to perfuse the branch vessels. However, deployment of branch stent-grafts has proven to be complicated and time-consuming thus increasing the risk of the procedure.

To avoid custom fabrication of main stent-grafts, side openings in the main stent-graft may be formed in situ. Illustratively, the main stent-graft is placed in the main vessel, e.g., the aorta, to exclude an aneurysm. Side openings are made in situ to correspond to and perfuse the branch vessels.

However, deployment of the main stent-graft temporarily interrupts perfusion to the branch vessels until the side openings are formed in the main stent-graft. To illustrate, perfusion to the brain via the carotids cannot be interrupted for any significant interval of time. Accordingly, the formation of side openings in a main stent-graft in situ is a complicated and risky procedure.

SUMMARY OF THE INVENTION

In accordance with one example, a method of deploying an eversible branch stent-graft includes deploying the eversible branch stent-graft into a main vessel such that a collateral opening in a main stent-graft of the eversible branch stent-graft is aligned with an ostium of a branch vessel emanating from the main vessel. A branch anchor suture is removed to release a protruding end of a branch stent-graft from a proximal end of the main stent-graft. A branch stent ring suture threaded through the outer exposed crowns of an outer stent ring of the branch stent-graft is grasped and pulled through the collateral opening to evert the branch stent-graft into the branch vessel.

As set forth above, the protruding end of the branch stent-graft is initially located at the proximal end of the main stent-graft. Further, the collateral opening is aligned with the ostium of the branch vessel. Accordingly, a portion of the blood flow through the main vessel enters the branch stent-graft at the protruding end, travels through a branch lumen of the branch stent-graft, exits through the collateral opening and passes into the branch vessel.

In this manner, the branch vessel is perfused through the branch stent-graft during the entire procedure of deploying the everted branch stent-graft. Accordingly, perfusion to the brain via the carotids is not interrupted for any significant interval of time reducing the complexity and risk of the procedure. Further, deployment of the branch stent-graft into the branch vessel is simple and direct.

Embodiments are best understood by reference to the following detailed description when read in conjunction with the accompanying drawings.

BRIEF DESCRIPTION OF THE DRAWINGS

Common reference numerals are used throughout the drawings and detailed description to indicate like elements.

DETAILED DESCRIPTION

Figure 2:
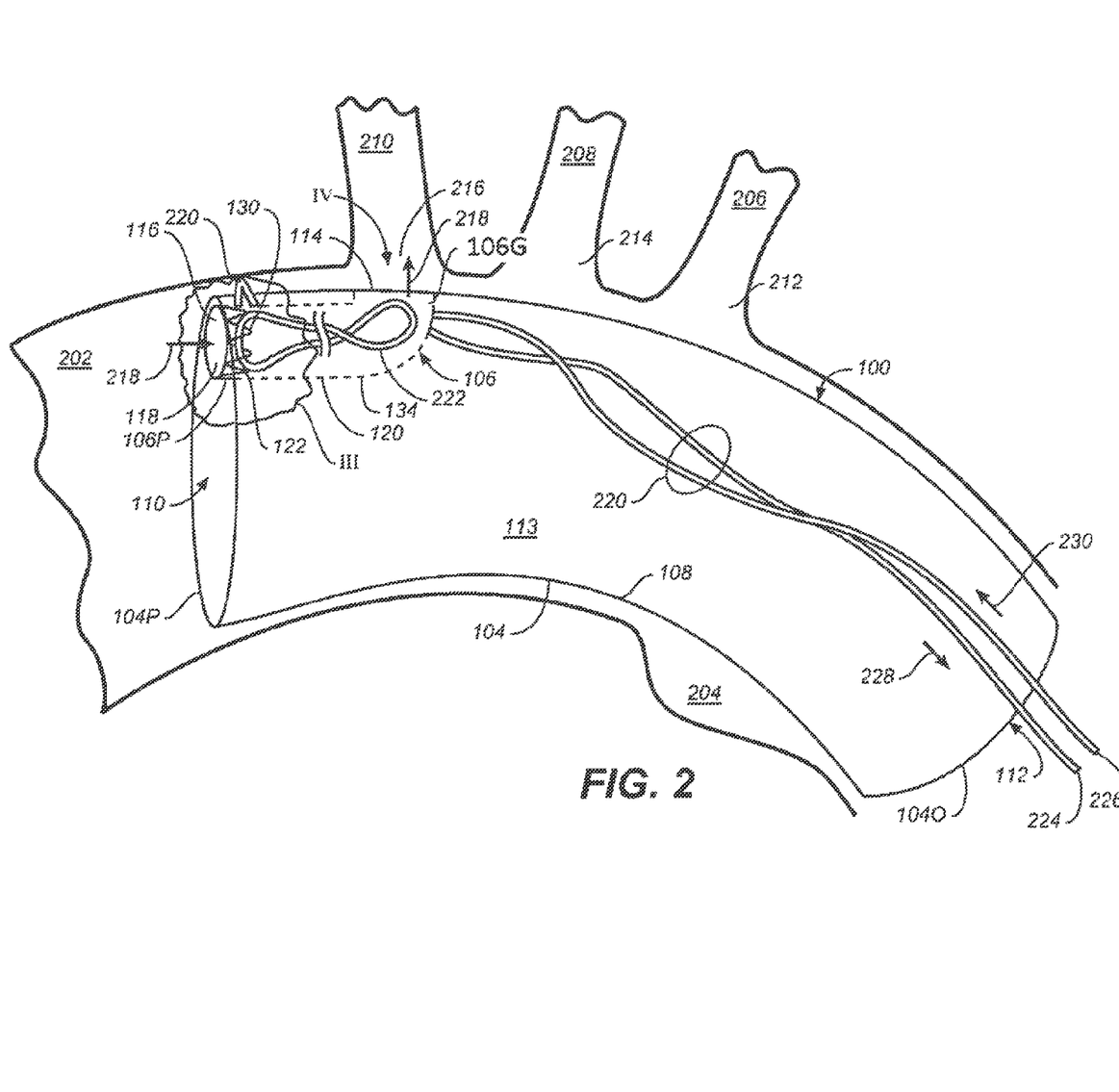
FIG. 2 is a schematic cross-sectional view of the eversible branch stent-graft of FIG. 1 being deployed in a main vessel in accordance with one example.

Referring to FIG. 2, a method includes deploying an eversible branch stent-graft 100 into a main vessel 202 such that a collateral opening 114 in a main stent-graft 104 of eversible branch stent-graft 100 is aligned with an ostium 216 of a branch vessel 210 emanating from main vessel 202. A branch anchor suture 220 is removed to release a protruding end 106P of a branch stent-graft 106 from a proximal end 104P of main stent-graft 104.

Figure 3:
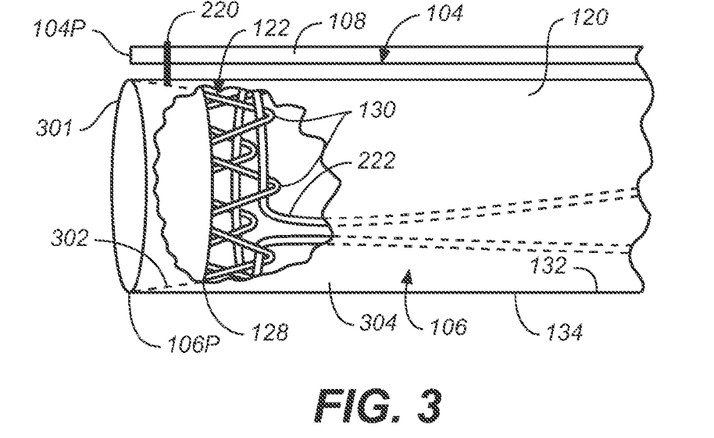
FIG. 3 is an enlarged schematic cross-sectional view, partially cutaway, of a region III of the eversible branch stent-graft of FIG. 2.
Figure 6:
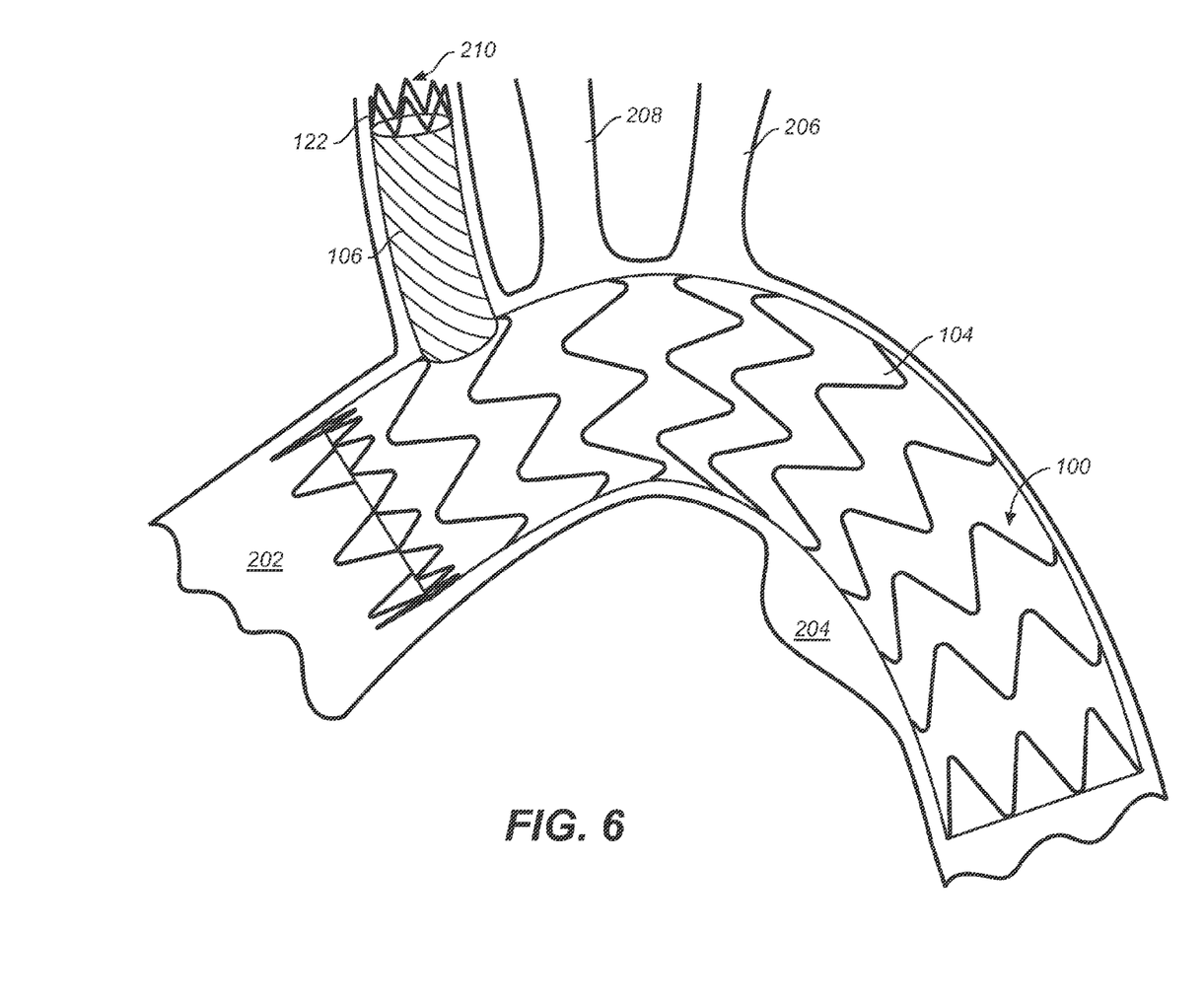
FIG. 6 is a side view of the eversible branch stent-graft deployed in the main vessel in accordance with one embodiment.

Referring now to FIGS. 2 and 3 together, a branch stent ring suture 222 threaded through outer exposed crowns 130 of an outer stent ring 122 of branch stent-graft 106 is grasped and pulled through collateral opening 114 to evert branch stent-graft 106 into branch vessel 210 as illustrated in FIG. 6.

Referring again to FIG. 2, protruding end 106P of branch stent-graft 106 is initially located at proximal end 104P of main stent-graft 104. Further, collateral opening 114 is aligned with ostium 216 of branch vessel 210. Accordingly, a portion of the blood flow through main vessel 202 enters branch stent-graft 106 at protruding end 106P, travels through a branch lumen 118 of branch stent-graft 106, exits through collateral opening 114 and passes into branch vessel 210 as indicated by the arrows 218.

In this manner, branch vessel 210 is perfused through branch stent-graft 106 during the entire procedure of deploying everted branch stent-graft 100. Accordingly, perfusion to the brain via the carotids is not interrupted for any significant interval of time reducing the complexity and risk of the procedure. Further, deployment of branch stent-graft 106 into branch vessel 210 is simple and direct.

Figure 1:
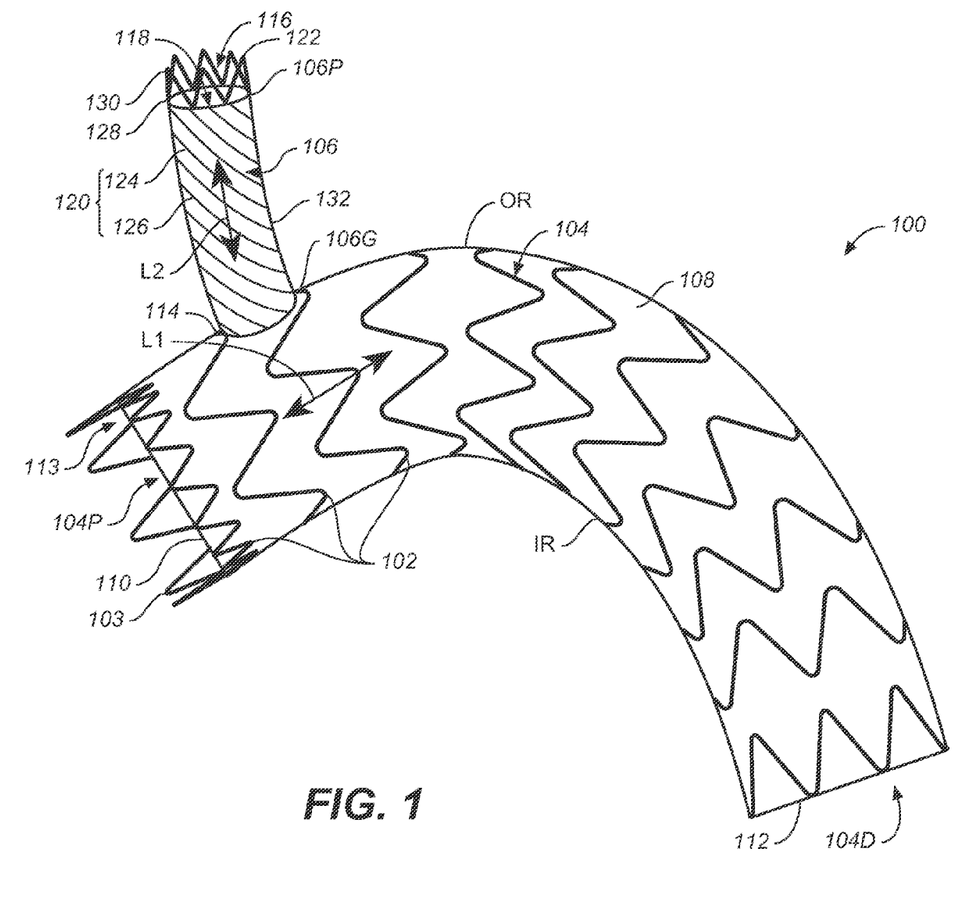
FIG. 1 is a side view of an eversible branch stent-graft in a deployed configuration in accordance with one embodiment.

More particularly, FIG. 1 is a side view of an eversible branch stent-graft 100, e.g., a thoracic aortic stent-graft, in a deployed configuration in accordance with one embodiment. Referring now to FIG. 1, eversible branch stent-graft 100 includes a plurality of primary stent rings 102 and a proximal exposed stent ring 103. Illustratively, primary stent rings 102 and proximal exposed stent ring 103 are self-expanding stent rings, e.g., formed of Nitinol.

Eversible branch stent-graft 100 includes a main stent-graft 104 and a branch stent-graft 106 coupled to one another. Main stent-graft 104, e.g., a Valiant® Stent Graft available from Medtronic, Inc., includes a graft material 108, e.g., graft cloth, and stent rings 102, 103 coupled, e.g., sewn, to graft material 108.

Main stent-graft 104 includes a proximal main opening 110 at a proximal end 104P of main stent-graft 104 and a distal main opening 112 at a distal end 104D of main stent-graft 104. Proximal exposed stent ring 103 is attached to graft material 108 at proximal end 104P of main stent-graft 104.

Further, main stent-graft 104 includes a longitudinal axis L1. A main lumen 113 is defined by main stent-graft 104 and extends generally parallel to longitudinal axis L1 and between proximal main opening 110 and distal main opening 112 of main stent-graft 104.

Main stent-graft 104 is curved, e.g., to accommodate the aortic arch. More particularly, main stent-graft 104 includes an inner radius of curvature IR and an outer radius of curvature OR. Graft material 108 of main stent-graft 104 is thus sometimes said to define a curved cylindrical surface. However, in another example, a main stent-graft similar to main stent-graft 104 is formed with a straight cylindrical graft material.

As used herein, the proximal end of a prosthesis such as a stent-graft is the end closest to the heart via the path of blood flow whereas the distal end is the end furthest away from the heart during deployment. In contrast and of note, the distal end of the catheter is usually identified to the end that is farthest from the operator (handle) while the proximal end of the catheter is the end nearest the operator (handle).

For purposes of clarity of discussion, as used herein, the distal end of the catheter is the end that is farthest from the operator (the end furthest from the handle) while the distal end of the prosthesis is the end nearest the operator (the end nearest the handle), i.e., the distal end of the catheter and the proximal end of the stent-graft are the ends furthest from the handle while the proximal end of the catheter and the distal end of the stent-graft are the ends nearest the handle. However, those of skill in the art will understand that depending upon the access location, the stent-graft and delivery system description may be consistent or opposite in actual usage.

Formed within main stent-graft 104 is a collateral opening 114. Collateral opening 114 is an opening in graft material 108. Generally, the area defined by collateral opening 114 lies upon the curved cylindrical surface defined by graft material 108 at or near the outer radius of curvature OR. Collateral opening 114 is described in greater detail below with reference to FIG. 4.

Branch stent-graft 106 is coupled, e.g. sewn, to main stent-graft 104 at a location between proximal main opening 110 and distal main opening 112 of main stent-graft 104. More particularly, a graft end 106G (sometimes called a proximal end in the deployed configuration of FIG. 1) of branch stent-graft 106 is sewn to graft material 108 of main stent-graft 104 around collateral opening 114, which forms an inner opening (sometimes called a proximal opening in the deployed configuration of FIG. 1) for branch stent-graft 106. In the example illustrated in FIG. 1, branch stent-graft 106 is attached between the second and third most proximal stent rings 102.

Branch stent-graft 106 further includes an outer opening 116 at a protruding end 106P (sometimes called a distal end in the deployed configuration of FIG. 1) of branch stent-graft 106. Further, branch stent-graft 106 includes a longitudinal axis L2 substantially perpendicular to longitudinal axis L1 of main stent-graft 104. A branch lumen 118 is defined by branch stent-graft 106 and extends generally parallel to longitudinal axis L2 and between collateral opening 114 and outer opening 116 of branch stent-graft 106.

Branch stent-graft 106 includes a tubular graft member 120 and an outer stent ring 122 (sometimes called a distal stent ring in the deployed configuration of FIG. 1). In one example, tubular graft member 120 is a graft material braid 124 with several strands of wire 126, e.g., Nitinol wire, incorporated into the braid. An example of tubular graft member 120 includes braided polyester along with a Nitinol wire for stability, available from Secant Medical. The tubular graft member 120 may also comprise a woven cloth tube. The tube may be woven in a tubular shape, or the tube may be created from a flat rectangle of cloth with opposite edges joined by any appropriate means.

Outer stent ring 122 is coupled, e.g., sewn, to tubular graft member 120 at protruding end 106P of branch stent-graft 106. An example of outer stent ring 122 includes a bare nitinol spring as is known in the art. As discussed in greater detail below, outer stent ring 122 is a sinusoidal pattern having inner attached crowns 128 and outer exposed crowns 130. Crowns 128, 130 are sometimes called the minima and maxima, or peaks and valleys of outer stent ring 122.

Inner attached crowns 128 are coupled, e.g., sewn, to tubular graft member 120 at protruding end 106P of branch stent-graft 106 thus coupling outer stent ring 122 to tubular graft member 120. Outer exposed crowns 130 are exposed, i.e., project freely from tubular graft member 120 facilitating capture and manipulation with a branch stent ring suture as discussed further below. The outer stent ring 122 also establishes fixation and seal when finally positioned.

FIG. 2 is a schematic cross-sectional view of eversible branch stent-graft 100 of FIG. 1 being deployed in a main vessel 202 in accordance with one example. In FIG. 2, primary stent rings 102 and proximal exposed stent ring 103 are not illustrated for clarity of presentation. Further, main stent-graft 104 is illustrated as being transparent to illustrate features therein, however, it is to be understood that main stent-graft 104 may be opaque in actual usage.

Referring now to FIG. 2, eversible branch stent-graft 100 is deployed into a main vessel 202 using any one of a number of well known techniques, the particular delivery/deployment technique used is not essential.

Further, as illustrated in FIG. 2, eversible branch stent-graft 100 is in a pre-deployment configuration, sometimes called a delivery configuration. In the pre-deployment configuration, branch stent-graft 106 is everted (turned inside out) inside of main lumen 113 of main stent-graft 104. More particularly, graft end 106G of branch stent-graft 106 remains attached to graft material 108 of main stent-graft 104 as discussed above. Protruding end 106P is located within proximal main opening 110 and at proximal end 104P of main stent-graft 104.

Main vessel 202, e.g., the aorta, includes an aneurysm 204, e.g., a thoracic aortic aneurysm (TAA). Generally, main stent-graft 104 seals against main vessel 202 above and below, e.g., proximally and distally to, aneurysm 204. Accordingly, fluid flows through main lumen 113 of main stent-graft 104 thus bypassing and excluding aneurysm 204.

Branching off main vessel 202 are three branch vessels 206, 208, 210, e.g., the subclavian, the common carotid, and the brachiocephalic trunk. In the example illustrated in FIG. 2, main stent-graft 104 is deployed proximally to branch vessels 206, 208, 210 covering (over) the ostia (plural of ostium) 212, 214, 216 of branch vessels 206, 208, 210, respectively.

However, branch vessels 206, 208, 210 are perfused through branch stent-graft 106. More particularly, prior to deployment of eversible branch stent-graft 100, a well known preliminary procedure to create a right-left carotid bypass and a left-carotid-subclavian bypass is performed. This preliminary procedure insures that perfusion to branch vessel 210 perfuses branch vessels 206, 208. Stated another way, this preliminary procedure provides that a portion of the blood flow into branch vessel 210 is redirected to branch vessels 206, 208 as those of skill in the art will understand.

As set forth above, protruding end 106P and thus outer opening 116 is located within proximal main opening 110. Further, eversible branch stent-graft 100 is deployed such that collateral opening 114 is aligned with ostium 216 of branch vessel 210. Accordingly, a portion of the blood flow through main vessel 202 enters outer opening 116 at protruding end 106P of branch stent-graft 106, travels through branch lumen 118, exits through collateral opening 114 and into branch vessel 210 as indicated by the arrows 218.

In this manner, branch vessel 210 and thus all of branch vessels 206, 208, 210 are perfused through branch stent-graft 106 during the entire procedure of deploying eversible branch stent-graft 100. Accordingly, perfusion to the brain via the carotids is not interrupted for any significant interval of time reducing the complexity and risk of the procedure.

FIG. 3 is an enlarged cross-sectional view, partially cutaway, of a region III of eversible branch stent-graft 100 of FIG. 2. Referring now to FIGS. 2 and 3 together, eversible branch stent-graft 100 includes a branch anchor suture 220 and a branch stent ring suture 222.

Branch anchor suture 220 is a single continuous suture that sutures (attaches) protruding end 106P of branch stent-graft 106 to proximal end 104P of main stent-graft 104.

Branch anchor suture 220 extends through graft material 108 of main stent-graft 104 and through tubular graft member 120 of branch stent-graft 106, i.e., is stitched to graft material 108 and tubular graft member 120. In one example, branch anchor suture 220 is a single stitch between graft material 108 and tubular graft member 120 facilitating easy removal of branch anchor suture 220.

As branch anchor suture 220 is a single continuous suture, branch anchor suture 220 has two ends 224, 226. Branch anchor suture 220 extends proximally (towards the handle) from protruding end 106P of branch stent-graft 106 and proximal end 104P of main stent-graft 104, though main lumen 113, through the lumen of the graft cover (not shown) and exits the patient, e.g., through a luer fitting. More particularly, at least one of ends 224, 226 exits the patient.

To remove branch anchor suture 220 thus releasing protruding end 106P of branch stent-graft 106 from proximal end 104P of main stent-graft 104, end 224 (or end 226) is pulled proximally as indicated by arrow 228 causing end 226 (or end 224) to move distally as indicated by arrow 230. End 226 (or end 224) thus slips out of both graft material 108 of main stent-graft 104 and tubular graft member 120 of branch stent-graft 106 releasing protruding end 106P of branch stent-graft 106 from proximal end 104P of main stent-graft 104. Branch anchor suture 220 is pulled until end 226 (or end 224) is removed from the patient thus completely removing branch anchor suture 220.

In light of this disclosure, those of skill in the art will understand that any one of a number of delivery catheters can be designed to facilitate removal of branch anchor suture 220 and the particular catheter used is not essential.

In the view of FIGS. 2 and 3, branch stent-graft 106 is everted (inside out), whereas in the view of FIG. 1, branch stent-graft 106 in uneverted (right side out). To further illustrate, referring to FIGS. 1, 2 and 3 together, branch stent-graft 106 includes a first surface 132 and a second surface 134, e.g., cylindrical surfaces opposite one another. In the deployed configuration as illustrated in FIG. 1, first surface 132 is the outer surface of branch stent-graft 106. In contrast, in the delivery configuration as illustrated in FIGS. 2-3, second surface 134 is the outer surface of branch stent-graft 106.

Further, as illustrated in FIGS. 1, 2, and 3, the orientation and configuration of outer stent ring 122 is maintained uneverted. In the delivery configuration the tubular graft member 120 of the branch stent graft 106 is everted around the stent ring 122, upon deployment of the main stent graft 104, the stent ring 122 keeps the tubular graft member 120 of the branch stent graft 106 open to perfuse the branch vessel 210 during the time of branch manipulation and deployment. During the process of branch stent graft 106 deployment the stent ring 122 is pulled through the everted tubular graft member 120 to turn it right side out as it follows the stent ring 122 out the collateral opening 114. Paying particular attention to FIG. 3, tubular graft member 120 is folded over at protruding end 106P in the delivery configuration. More particularly, tubular graft member 120 is folded over at a fold 301 such that a first portion 302 of tubular graft member 120 extends back inside of the remaining second portion 304 of tubular graft member 120. Portion 302 is attached, e.g., sewn, to inner attached crowns 128 of outer stent ring 122.

Figure 4:
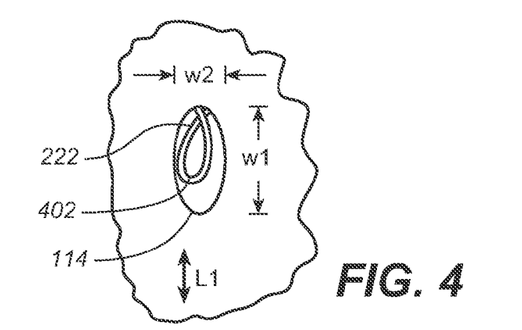
FIG. 4 is a view of a collateral opening of the eversible branch stent-graft seen as viewed along line IV of FIG. 2.

FIG. 4 is a view of collateral opening 114 of eversible branch stent-graft 100 taken along the line IV of FIG. 2. As illustrated in FIG. 4, collateral opening 114 is ellipsoidal having a greater first width W1 parallel to longitudinal axis L1 than a second width W2 perpendicular to longitudinal axis L1. The ellipsoidal shape of collateral opening 114 has been found to produce a lumen of the largest cross sectional area branch stent-graft 106 to make the turning of the tubular graft member 120 right side out easier than when a circular opening known in the art is used.

Referring now to FIGS. 2, 3, and 4 together, branch stent ring suture 222 is a closed loop of suture, i.e., has no free ends. Branch stent ring suture 222 has been threaded through outer exposed crowns 130 of outer stent ring 122. Branch stent ring suture 222 is packed in the everted tubular graft member 120 and extends from outer stent ring 122, through branch stent-graft 106 to have a grasping end loop 402 adjacent collateral opening 114. In one embodiment, to facilitate the eversion, grasping end loop 402 of branch stent ring suture 222 is performed, sometimes called snared, with a tool advanced through branch vessel 210, e.g., via an introducer in the carotid or brachial artery. The tool can take any one of a number of shapes to snare grasping end loop 402 of branch stent ring suture 222, e.g., a hook shaped tool, a helical tool, or other shaped tool. The particular tool used is not essential to this example. In one example, end loop 402 of branch stent ring suture 222 is located within branch stent-graft 106 and thus the tool must be advanced through collateral opening 114 to grasp end loop 402 and pull it out of the branch stent graft 106. The length of the branch stent ring suture 222 loop once extended is long enough to extend through a patient's anatomy to and out the carotid or brachial artery access opening. In one configuration once the packed loop is extended outside the patient's body thereby putting the outer stent ring 122 of the branch stent graft 106 under the direct control of the implanting physician. In another configuration the packed loop is long enough to be grabbed securely by the snare catheter, which after branch graft deployment can hold the loop securely as it is cut by that or another catheter to release tension on the loop and safely extract the remnant of the loop from the patient's body.

Once the end loop 402 of branch stent ring suture 222 is under control the physician, the protruding end 106P of branch stent-graft 106 can be released from main stent-graft 104 by removal of branch anchor suture 220 as discussed above, As the branch anchor suture 220 is released, branch stent-graft 106 begins to self-evert (turn inside out) due to the flow of blood through branch stent-graft 106 in one example. The amount of self-eversion (turning inside out) depends upon the particular application and can vary from complete eversion to no eversion. Simultaneously with the self eversion, the physician can pull on the branch stent ring suture 222 to guide the branch stent ring 130 to the collateral opening 114.

Once the branch anchor suture 220 loop is free of the branch stent graft 106, the branch stent ring suture 222 is then further pulled, i.e., through tubular graft member 120 and out of collateral opening 114, causing branch stent-graft 106 to evert into branch vessel 210 as explained in greater detail below with reference to FIG. 5.

Figure 5:
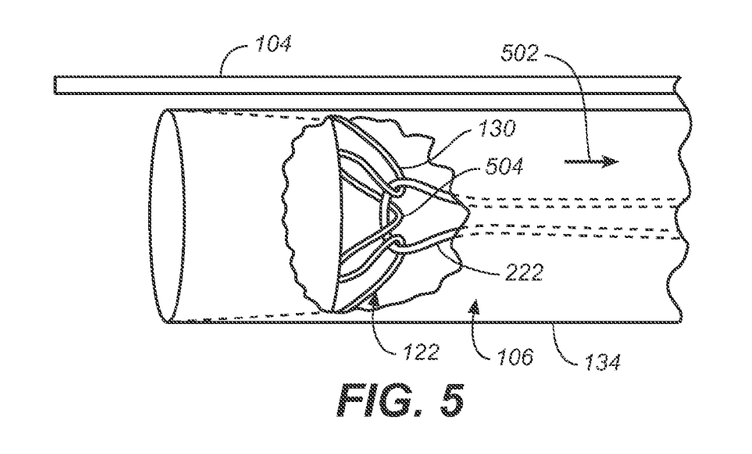
FIG. 5 is an enlarged cross-sectional view, partially cutaway, of the eversible branch stent-graft of FIG. 3 during eversion of a branch stent-graft.

FIG. 5 is an enlarged schematic cross-sectional view, partially cutaway, of eversible branch stent-graft 100 of FIG. 3 during eversion of branch stent-graft 106. As illustrated in FIG. 5, retraction of branch stent ring suture 222 in the direction of arrow 502 causes outer exposed crowns 130 to be pulled together in apposition due to the application of tension. This causes outer stent ring 122 to assume a conical shape, having a leading apex 504. This conical shape, sometimes called a conical leading profile, enhances passing of outer stent ring 122 though tubular graft member 120, through collateral opening 114 and into branch vessel 210 as illustrated in FIG. 6.

FIG. 6 is a side view of eversible branch stent-graft 100 deployed in main vessel 202 in accordance with one embodiment. Referring now to FIGS. 5 and 6 together, once branch stent ring suture 222 is pulled to completely extend branch stent-graft 106 within branch vessel 210, branch stent-graft 106 is completely everted and has an absence of folds, i.e., no portion of branch stent-graft 106 extends back into itself. Branch stent ring suture 222 is cut and removed from outer stent ring 122 through branch vessel 210. Accordingly, deployment of branch stent-graft 106 into branch vessel 210 is simple and direct.

Although perfusion of and deployment into branch vessel 210 is set forth above, in other examples, branch stent-graft 106 is deployed into other branch vessels, e.g., into branch vessel 206 or branch vessel 208.

In one example, completion of the procedure is accomplished by deploying a Palmaz stent within branch stent-graft 106 well distal to the junction between main stent-graft 104 and branch stent-graft 106. This ensures that this junction is mobile and deformable to accommodate the well documented, large displacement motions of the ascending aorta during the cardiac cycle.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A method of deploying an eversible branch stent-graft comprising:
    deploying said eversible branch stent-graft into a main vessel such that a collateral opening in a main stent-graft portion of said eversible branch stent-graft is aligned with an ostium of a branch vessel emanating from said main vessel and such that a branch stent-graft portion of said eversible branch stent-graft is in a delivery configuration within a lumen of said main stent-graft portion;
    grasping a branch stent ring suture threaded though outer exposed crowns of an outer stent ring of said branch stent-graft portion;
    removing a branch anchor suture to release a protruding end of said branch stent-graft portion from a proximal end of said main stent-graft; and
    pulling said branch stent ring suture through said collateral opening to evert said branch stent-graft portion by turning an inner surface of said branch stent-graft portion outward such that said branch stent-graft portion is in a deployed configuration and extends from said collateral opening into said branch vessel.

2. The method of claim 1, wherein in the delivery configuration a portion of a blood flow through said main vessel enters said branch stent-graft portion at said protruding end, travels through a branch lumen defined by said inner surface of said branch stent-graft portion in the delivery configuration, exits through said collateral opening and into said branch vessel to perfuse said branch vessel.

3. The method of claim 1, wherein said removing a branch anchor suture comprises pulling a first end of said branch anchor suture to cause a second end of said branch anchor suture to slip out of said protruding end of said branch stent-graft portion and said proximal end of said main stent-graft portion.

4. The method of claim 1, wherein said branch stent-graft portion comprises a first surface and a second surface, wherein prior to said pulling, said first surface is said inner surface and said second surface is an outer surface of said branch stent-graft portion, and wherein after said pulling, said first surface is said outer surface and said second surface is said inner surface of said branch stent-graft portion.

5. The method of claim 1, wherein said branch stent-graft portion comprises a tubular graft member attached to said outer stent ring, wherein prior to said pulling, said tubular graft member is folded over at a fold such that a first portion of said tubular graft member extends back inside a remaining second portion of said tubular graft member, said first portion being attached to said outer stent ring.

6. The method of claim 5 wherein said pulling comprises passing said outer stent ring through said tubular graft member.

7. The method of claim 6 wherein said pulling comprises causing said outer exposed crowns of said outer stent ring to be pulled together in apposition.

8. The method of claim 7 wherein said outer stent ring assumes a conical shape having a leading apex when said outer exposed crowns are pulled together in apposition.

9. The method of claim 5 wherein said tubular graft member comprises:
a graft material braid; and
several strands of wire incorporated into said graft material braid.

10. The method of claim 1 further comprising cutting said branch stent ring suture and removing said branch stent ring suture from said outer stent ring.

11. A method of deploying an eversible branch stent-graft comprising:
positioning a branch stent-graft in a delivery configuration within a lumen of a main stent-graft, wherein in the delivery configuration a first end of the branch stent-graft is disposed proximate to a proximal end of the main stent-graft and a second end of the branch stent-graft is attached proximate to a collateral opening of the main stent-graft;
deploying within a main vessel the main stent-graft with the branch stent-graft in the delivery configuration, wherein the collateral opening in the main stent-graft is aligned with an ostium of a branch vessel; and
pulling the first end of the branch stent-graft through the collateral opening of the main stent-graft to evert the branch stent-graft into a deployed configuration, wherein in the deployed configuration the branch stent-graft extends from the collateral opening of the main stent-graft into the branch vessel.

12. The method of claim 11, wherein the branch stent-graft includes a first surface and a second surface, and
wherein prior to the step of pulling, the first surface is an inner surface and the second surface is an outer surface of the branch stent-graft, and
wherein after the step of pulling, the first surface is the outer surface and the second surface is the inner surface of the branch stent-graft.

13. The method of claim 11, wherein the branch stent-graft comprises an outer stent ring attached to a tubular graft member at an end thereof, and
wherein in the delivery configuration the end of the tubular graft member is folded over such that the outer stent ring is within a lumen defined by a first surface of the tubular graft material.

14. The method of claim 13, wherein the step of pulling further comprises advancing the outer stent ring through the lumen of the tubular graft member and out of the collateral opening of the main stent-graft to thereby turn the first surface of the tubular graft member outward to evert the branch stent-graft.

15. The method of claim 14, wherein the outer stent ring anchors the first end of the branch stent-graft within the branch vessel.

16. The method of claim 14, wherein the step of pulling further comprises advancing the outer stent ring through the lumen of the tubular graft member by pulling on a branch stent ring suture threaded though outer exposed crowns of the outer stent ring of the branch stent-graft.

17. The method of claim 11, further comprising:
removing a branch anchor suture to release the first end of the branch stent-graft from the proximal end of the main stent-graft.

18. The method of claim 11, wherein in the delivery configuration blood flow through the main vessel enters the first end of the branch stent-graft, travels through a branch lumen defined by the branch stent-graft in the delivery configuration, exits through the collateral opening of the main stent-graft and enters into the branch vessel to thereby perfuse the branch vessel.

* * * * *